US005832095A

United States Patent [19]

Daniels

[11] Patent Number: 5,832,095

[45] Date of Patent: Nov. 3, 1998

[54] NOISE CANCELING SYSTEM

[75] Inventor: Mark A. Daniels, Manlius, N.Y.

[73] Assignee: Carrier Corporation, Syracuse, N.Y.

[21] Appl. No.: 731,788

[22] Filed: Oct. 18, 1996

[51] Int. Cl.[6] .......... H03B 29/00; A61F 11/06

[52] U.S. Cl. .......... 381/71.5; 381/71.14; 381/94.2

[58] Field of Search .......... 381/71, 94, 66

[56] References Cited

U.S. PATENT DOCUMENTS

| | | | |
|---|---|---|---|
| 4,044,203 | 8/1977 | Swinbanks | 381/71.5 |
| 4,636,586 | 1/1987 | Schiff | 381/71.11 |
| 4,677,676 | 6/1987 | Eriksson | 381/71 |
| 4,683,590 | 7/1987 | Miyoshi et al. | 381/71.12 |
| 4,783,817 | 11/1988 | Hamada et al. | 381/71.5 |
| 4,815,139 | 3/1989 | Eriksson | 381/71.5 |
| 4,829,590 | 5/1989 | Ghose | 381/71.8 |
| 4,837,834 | 6/1989 | Allie | 381/71.11 |
| 4,987,598 | 1/1991 | Eriksson | 381/71 |
| 5,029,218 | 7/1991 | Nagayasu | 381/71.14 |
| 5,119,427 | 6/1992 | Hersh et al. | 381/71.14 |
| 5,206,911 | 4/1993 | Eriksson | 381/71 |
| 5,283,834 | 2/1994 | Goodman et al. | 381/71.5 |
| 5,347,585 | 9/1994 | Taki et al. | 381/71.5 |
| 5,377,275 | 12/1994 | Suzuki | 381/71.8 |
| 5,418,873 | 5/1995 | Eriksson | 381/71.5 |
| 5,420,932 | 5/1995 | Goodman | 381/71.5 |
| 5,499,302 | 3/1996 | Nagami et al. | 381/71.11 |
| 5,526,292 | 6/1996 | Hodgson et al. | 381/71.4 |
| 5,602,926 | 2/1997 | Ohashi et al. | 381/71.5 |
| 5,689,572 | 11/1997 | Ohki et al. | 381/94.1 |
| 5,713,438 | 2/1998 | Rossetti et al. | 381/71.1 |
| 5,748,750 | 5/1998 | L'Esperance et al. | 381/71.5 |

*Primary Examiner*—Curtis A. Kuntz
*Assistant Examiner*—Xu Mei

[57] ABSTRACT

Two microphones spaced along a duct of an air conditioning system provide inputs to circuitry whereby the noise being generated is distinguished from reflected noise. The circuitry imposes a time delay corresponding to the time required for generated noise to pass from the upstream microphone to a canceling speaker. The canceling speaker is driven by the circuitry, subject to the time delay, such that noise at the speaker is canceled by the appropriately driven speaker. In a preferred embodiment movement of the speaker is sensed whereby the actual sound being produced can be compared with the sound required by the canceling speaker driving signal.

14 Claims, 5 Drawing Sheets

NOISE CANCELING SYSTEM

BACKGROUND OF THE INVENTION

In conventional active noise cancellation (ANC)schemes, the noise from the noise source is sensed and, responsive thereto, a loudspeaker located downstream is activated to produce a noise canceling signal. A dynamic pressure sensor, such as a microphone, located downstream of the loudspeaker senses the resultant noise, after noise canceling has taken place, and provides a feedback signal to the loudspeaker activation circuitry to correct the noise canceling signal from the speaker. A major complication of all active noise systems is that the duct characteristics are superimposed upon the noise canceling process which includes noise emitted and reflected back from the noise canceling loudspeaker towards the noise source. This additional noise will be sensed by the input microphone and, if not properly accounted for, will lead to system or feedback instabilities. So, as part of canceling the noise, it is necessary to identify and separate the reflected and generated noise from the control loudspeaker from that due to the noise source at the input microphone. Another drawback of conventional active noise cancellation schemes is the cumulative physical distances serially required between the input noise sensor, the noise canceler and the error noise sensor. The physical distances reflect the time required to sense the noise, process the information, produce a canceling signal and to sense the result of the canceling signal with each step corresponding to a time delay which requires additional physical distance. The reduction of these time delays would result in a reduced package size thereby making ANC more commercially attractive. Additionally, previous ANC systems have used adaptive infinite-impulse-response (IIR) filters to model feedback from the control loudspeaker to the output microphone. However, by their structure, IIR filters can be prone to stability problems.

SUMMARY OF THE INVENTION

A major improvement provided by the present invention is the elimination of an adaptive IIR filter structure. As a result, a system is provided which has a stabler control structure and greater system robustness. The present invention employs two cumulative structures that may be used individually, but preferably together. One feature is the use of two sensing microphones which are spaced apart a short distance along the duct thereby permitting the distinguishing of forward and reverse propagating waves in the duct. The second feature is to directly sense the velocity of the cone of the noise canceling loudspeaker which directly relates to the sound being produced. A signal proportional to the velocity of the cone of a noise canceling loudspeaker is compared to and subtracted from to the input of the speaker. This results in a dramatic improvement in the transient response of the loudspeaker together with a major group delay reduction with laboratory results of up to six milliseconds.

It is an object of this invention to produce a signal from a noise canceling loudspeaker that is directly proportional to the forward propagating acoustic pressure wave.

It is another object of this invention to permit the distinguishing of the forward propagating pressure wavefront which propagates from the source towards the ANC system and therefore eliminating the need for feedback modeling.

It is a further object of this invention to reduce the input microphone to loudspeaker distance or acoustic plant length required for active noise control related to ducts. These objects, and others as will become apparent hereinafter, are accomplished by the present invention.

Basically, a plurality of spaced sensing microphones are located at or near the noise source and the sensed signals are processed such that only the forward traveling wave component of the sound wave originating from the noise source is isolated and provided as an input to the canceling loudspeaker's driving circuitry. The velocity of the speaker cone of the canceling loudspeaker corresponds to the sound being produced by the canceling loudspeaker. By sensing the velocity of the speaker cone and comparing the sensed velocity to the driving signal the response time and distances can be shortened.

BRIEF DESCRIPTION OF THE DRAWINGS

For a fuller understanding of the present invention, reference should now be made to the following detailed description thereof taken in conjunction with the accompanying drawings wherein.

DESCRIPTION OF THE PREFERRED EMBODIMENT

Figure 1:
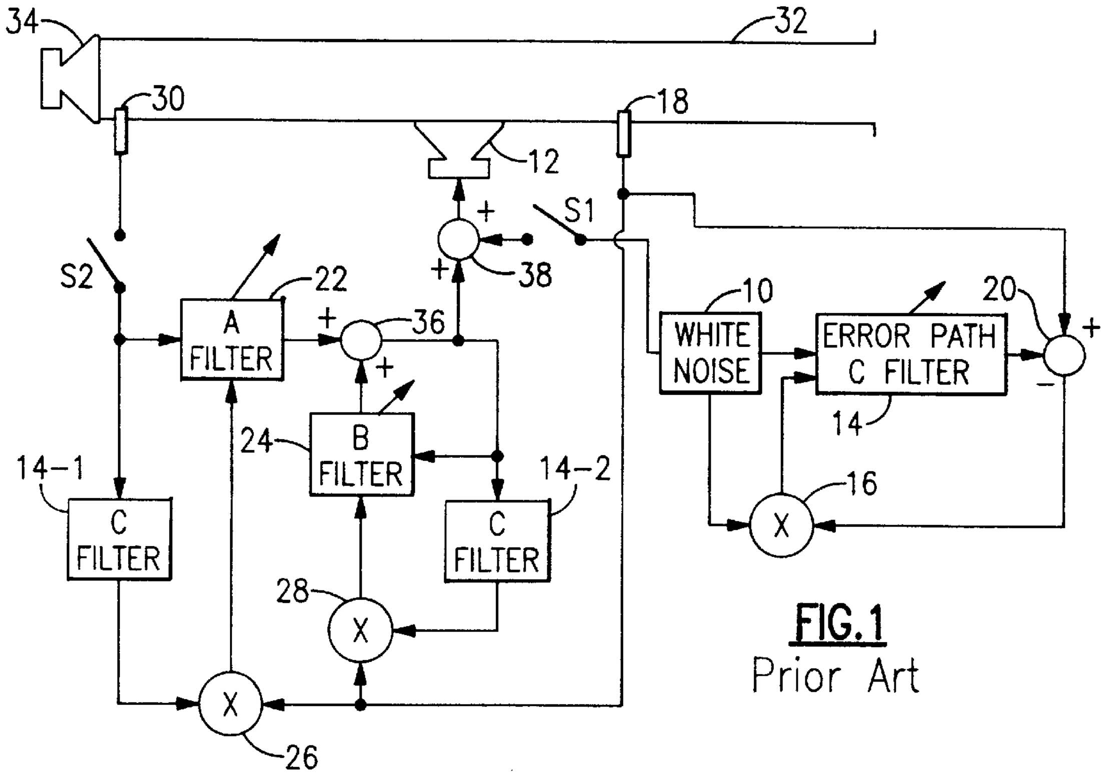
FIG.1 Prior Art
FIG. 1 is a schematic representation of a prior art noise canceling system.

FIG. 1 is based upon U.S. Pat. Nos. 4,677,676 and 4,677,677 which are drawn to an active noise cancellation system using an adaptive infinite-impulse-response (IIR) filter. Rather than trying to cancel the feedback sound component with special analog electronics and filters, the effects of both feedforward (sensing microphone to loudspeaker) and feedback (loudspeaker to sensing microphone) sound paths are modeled. Briefly, at start up, switch SI is closed connecting white noise source 10 to canceling loudspeaker 12 in addition to its connection to adaptive error path filter 14, and multiplier 16. The filter coefficients for filters 14-1 and 14-2 are zero at this time. Switch S2 is open so that white noise source 10 is providing the only input for loudspeaker 12. Filter 14 models the path from the input voltage to canceling loudspeaker 12, due to white noise source 10, to the output voltage measured by error microphone 18. The output of error microphone 18 and the output of filter 14 are supplied to adder 20. The output of adder 20 is supplied as an input to multiplier 16 and the output of multiplier 16 is supplied as a second input to filter 14. Filter 14 is required for system stability and, after identification of the error path, it is copied to filters 14-1 and 14-2 of the main control algorithm structure.

Switch S1 is opened and switch S2 is closed. The adaptive filters 22 and 24 are now identified while control is being performed at canceling loudspeaker 12. System performance is measured at error microphone 18 and fed back to the control system via multipliers 26 and 28 to update filters 22 and 24, respectively. Specifically, with switch S2 closed, sensing microphone 30 senses the noise produced in duct 32 by a noise source 34, represented by a loudspeaker, as well as from anti-noise or canceling loudspeaker 12 and provides an input representative of the sensed noise to filters 14-1 and 22. The filtered output of filter 14-1 is supplied as a second input to multiplier 26 whose output is supplied as a second input to filter 22. The output of filter 22 is supplied to adder 36 whose output is supplied to canceling loudspeaker 12 via adder 38, to filter 24 and to filter 14-2. The output of filter 14-2 is supplied as a second input to multiplier 28 and the output of multiplier 28 is supplied as a second input to filter 24. The output of filter 24 is supplied as a second input to adder 36. The structure of filters 14, 22 and 24 is generally implemented as transverse adaptive filters and the adaptation process is implemented using standard least-mean-square (LMS) techniques.

Figure 2:
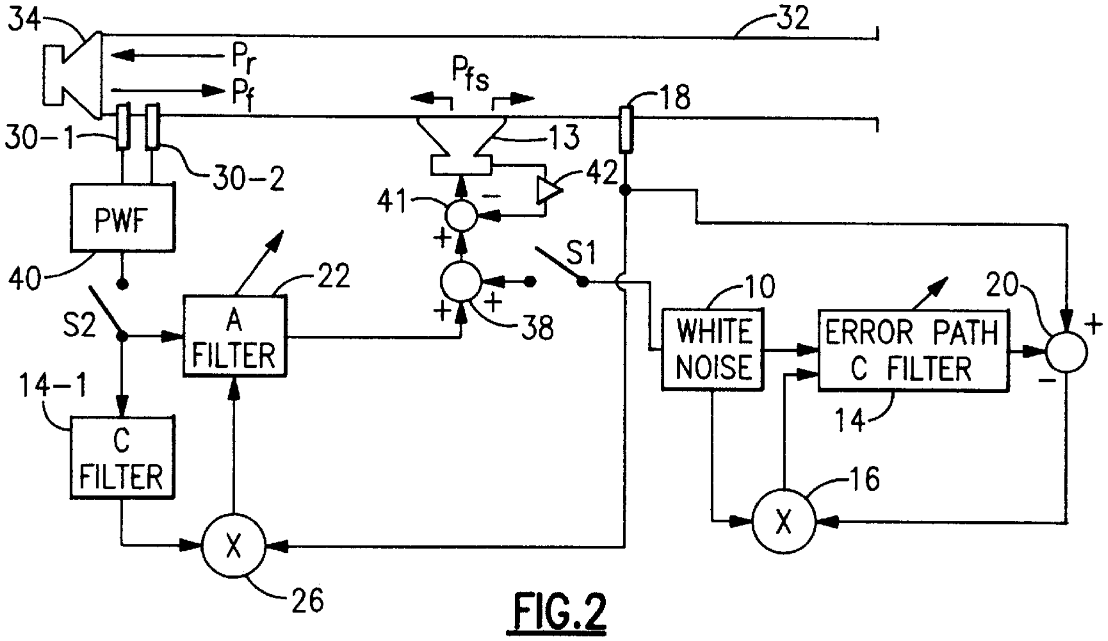
FIG. 2 is a schematic diagram of the noise canceling structure of the present invention.

In FIG. 2 structure corresponding to structure in FIG. 1 is given the same label and the numeral 32 generally designates a duct such as that used in the distribution of conditioned air. Mechanical equipment such as compressors and fans produce noise and are collectively illustrated as a loudspeaker 34 which is a noise source producing a forward pressure wave, $P_f$, which is proportional to the forward component of the acoustic particle velocity of the sound and is represented by an arrow in FIG. 2. In acoustics there are, primarily, two different velocities. The first is the particle velocity which is the actual molecular level velocity. The second is the velocity at which information propagates, i.e. the speed of sound. The first or particle velocity is based on the input or source conditions. The second velocity, or speed of sound, is based upon thermodynamic and physical properties of the fluid medium. Downstream noise sources as well as duct characteristics causing reflections produce a reverse pressure wave, $P_1$ which is also represented by an arrow in FIG. 2. Microphones 30-1 and 30-2 are located in duct 32 downstream of the noise source 34 in a spaced relationship relative to noise source 34. Because sensing microphones 30-1 and 30-2 are spaced from each other relative to noise source 34, they sense the forward and reverse pressure waves at different times and at different locations in their wave patterns whereby the two pressure waves can be distinguished by proper processing of the respective signals.

Figure 3:
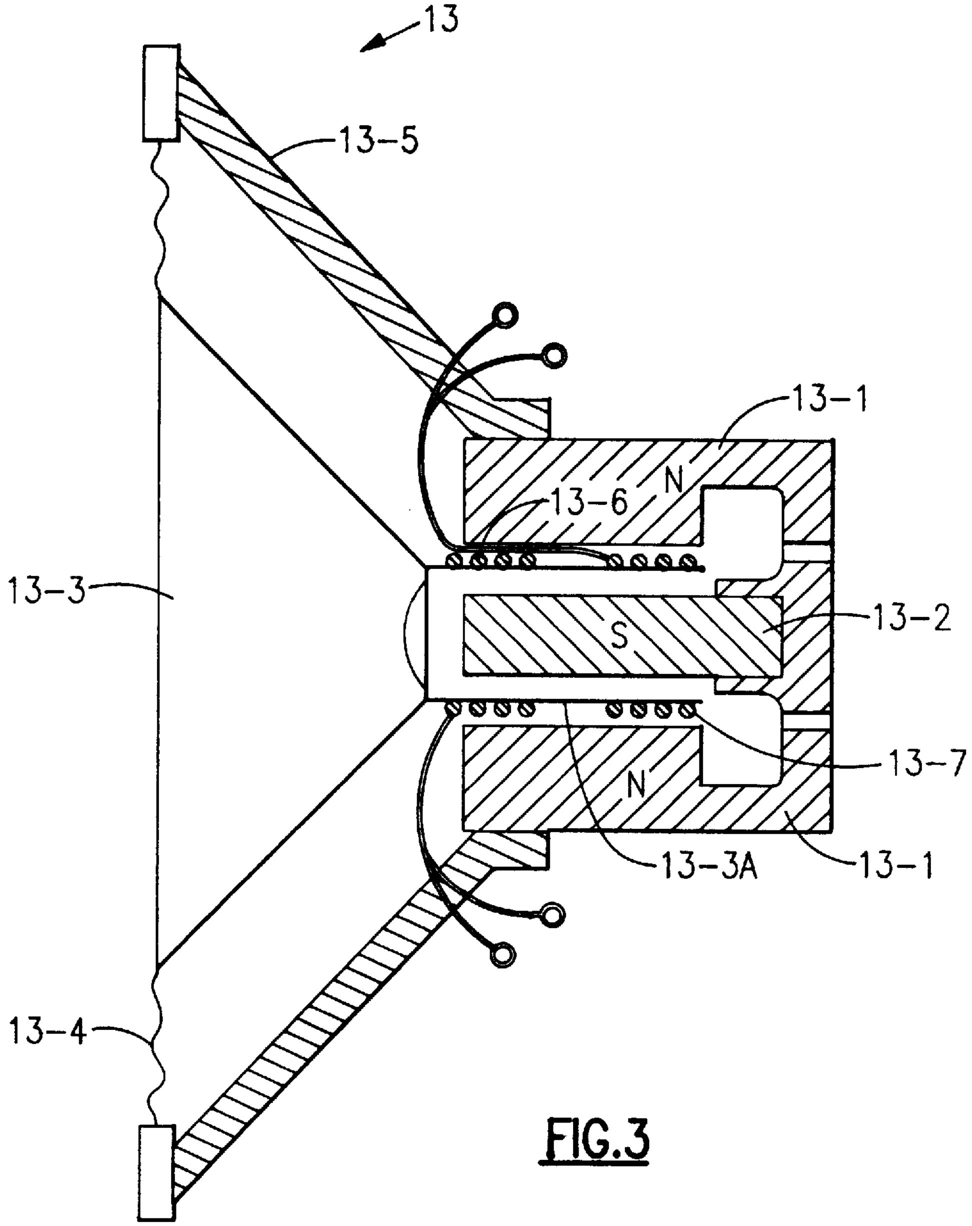
FIG. 3 is a sectional view of the canceling loudspeaker of the FIG. 2 device.

Canceling speaker 13 is operated to produce a sound to cancel the sound of noise source 34. Specifically, speaker 13 produces a forward pressure wave, $P_{fs}$, which is transmitted both upstream and downstream in duct 32 relative to speaker 13. Referring to FIG. 3, speaker 13 includes a permanent magnet having north poles 13-1 and a south pole 13-2. An air gap is defined between poles 13-1 and 13-2. Speaker cone 13-3 is supported on frame 13-5 by cone suspension 13-4. A portion, 13-3A, of cone 13-3 is located in the air gap and serves as a "former" for coils 13-6 and 13-7 which are glued to the former 13-3A of cone 13-3. The former 13-3A is essentially massless and provides stiffness to hold coils 13-6 and 13-7 which are movable therewith. When an alternating electric current is applied to coil 13-6 it is caused to move within the magnetic field in the air gap and carries cone 13-3 in its movement which results in the generation of noise/sound. Movement of coil 13-6 also causes the movement of coil 13-7 causing the inducing of a voltage in coil 13-7 with the induced voltage being proportional to the velocity of cone 13-3 and coils 136 and 13-7 which are moving as a unit.

Figure 4:
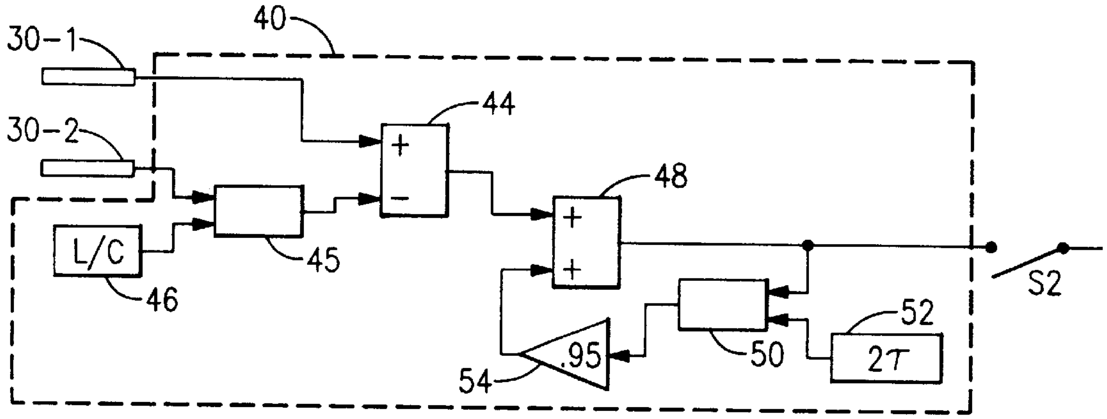
FIG. 4 is a schematic representation of the progressive wave filter of the FIG. 2 device.

Error microphone 18 is located in duct 32, spaced from speaker 13 and on the opposite side of speaker 13 from noise source 34. Sensing microphones 30-1 and 30-2, speaker 13 and error microphone 18 are connected through circuitry and coact to sense noise, cancel the sensed noise and correct the cancellation. Progressive wave filter (PWF) 40 is connected to sensing microphones 30-1 and 30-2 and, as best shown in FIG. 4, distinguishes the forward pressure wave, $P_f$, from the reverse pressure wave, $P_r$. In this implementation, flow effects are neglected and microphones 30-1 and 30-2 have the same gain sensitivities. The noise sensed by sensing microphones 30-1 and 30-2 is supplied as first inputs to adder 44 and time delay 45, respectively. Forward delay 46 provides a time delay, $\tau$, where $\tau = L/c$ and L is the separation distance of microphones 30-1 and 30-2 and c is the speed of sound in duct 32, as a second input to time delay 45. Delay 45 provides a second input to adder 44. The output of adder 44 is supplied as a first input to adder 48. The output of adder 48 represents the forward pressure wave, $P_f$, and is supplied via switch S2 to filters 14-1 and 22 and is supplied as a first input to time delay 50 in the feedback loop. Feedback delay 52, having a time delay of $2\tau$, provides a second input to delay 50. A loss term of 0.95 appears in the feedback loop as block 54 which receives an input from delay 50 and supplies a second input to adder 48. This small leakage in the feedback loop controls the stability of the filter 40 and keeps the filter gain at its poles within reasonable limits. This value was arbitrarily set to 0.95, however, any value between 0.9 and 0.99 could be chosen without appreciable loss in accuracy.

In FIG. 2, filters 22 and 14-1 receive the output of PWF 40, which represents $P_f$ at microphone 30-1, as an input. Filter 14-1 which is copied from filter 14, as described above with respect to FIG. 1, provides a first input to multiplier 26 and an output signal from error microphone 18 is provided as a second input to multiplier 26. The output of multiplier 26 is provided as a second input to filter 22. Filter 22 has an output representing the corrected forward pressure wave which is supplied via adder 38 to adder 41 as a first input. The output of filter 22 accounts for the time delay from microphone 30-1 to the canceling loudspeaker 13 and any anomaly associated with the frequency response of loudspeaker 13. The output of adder 38 which represents the driving force for speaker 13 and any gain corrections that may be required due to system effects is supplied to speaker 13 via adder 41. Referring again to FIG. 3, power supplied to coil 13-6 via adder 41 causes its movement and the movement of integral cone 13-3 which produces sound. Coil 13-7 moves therewith and the movement of coil 13-7 in the air gap between pole 13-1 and pole 13-2 induces a voltage in coil 13-7 which is related to the movement/velocity of coil 13-7. Since coil 13-7 is moving as a unit with cone 13-3 and coil 13-6, the voltage induced by movement of coil 13-7 is a direct indication of the velocity of movement of cone 13-3 and therefore the sound being produced by speaker 13 since the velocity of cone 13-3 is directly proportional to the forward pressure wave of the speaker ($P_{fs}$) caused by its movement. The voltage induced in coil 13-7 is sensed, passed through feedback gain step 42 as gain K and supplied as second input to adder 41 thereby correcting the driving signal for speaker 13 responsive to the actual operation of speaker 13.

In comparing FIGS. 1 and 2, it will be noted that the FIG. 2 device eliminates filters 14-2 and 24 and multiplier 28 and adder 36.

Figure 5:
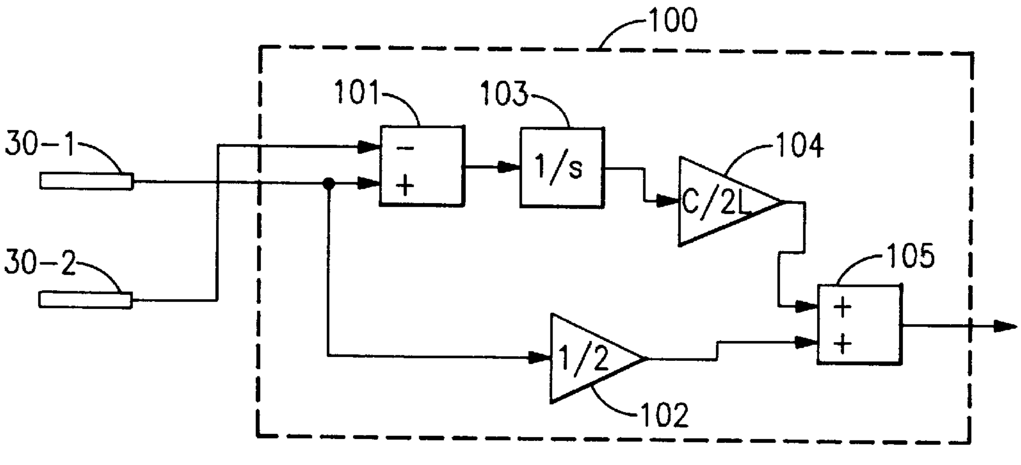
FIG. 5 is a schematic representation of a forward pressure wave approximation filter which is an alternative to the FIG. 4 embodiment.

Turning now to FIG. 5, the progressive wave filter 40, PWF, of FIG. 4 can be replaced with forward pressure wave approximation filter 100. The noise sensed by sensing microphone 30-1 is supplied as a first input to adder 101 and as an input to divider 102. The noise sensed by sensing microphone 30-2 is supplied as a second input to adder 101.

The output of adder 101 is supplied to integrator 103 which supplies an input to divider 104. The outputs of dividers 104 and 102 are supplied as first and second inputs, respectively, to adder 105 which has an output $P_f$. The embodiment of the PWF 40 described in FIG. 4 reduces to that in FIG. 5 when kL <λ/8 where k is the acoustic wave number, L is the separation distance between microphones 30-1 and 30-2, and λ=the acoustic wavelength.

Figure 6:
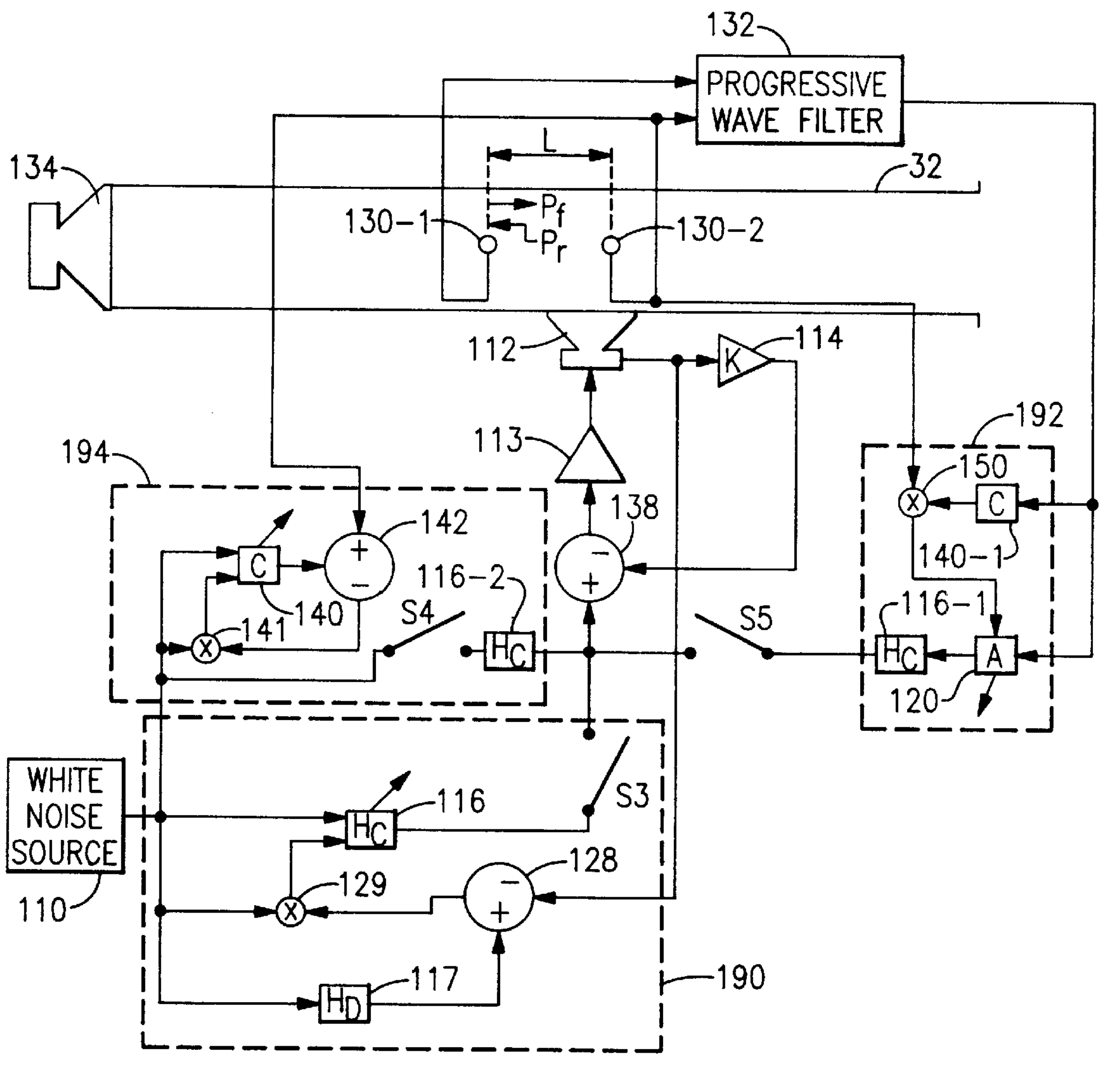
FIG. 6 is a schematic representation of a system using a digital implementation of the controller.
Figure 7:
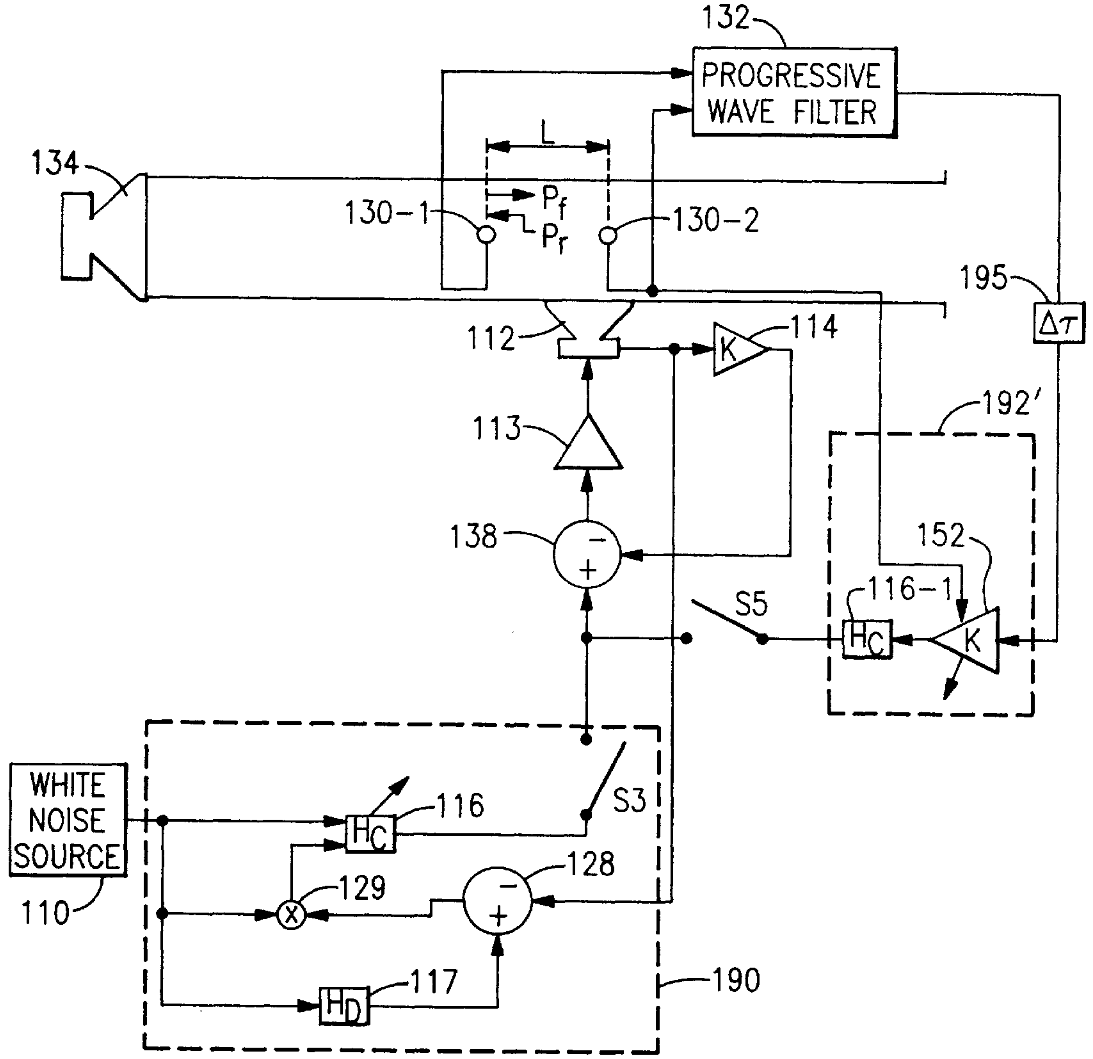
FIG. 7 is a schematic representation of a system using an analog implementation of the controller.

Before proceeding with the description of the embodiments of FIGS. 6 and 7, note their common servo (feedback) mechanism at the loudspeaker 112 and power amplifier 113. The servo mechanism provides a feedback signal that is proportional to the loudspeaker's cone velocity through feedback gain stage 114, having a gain K.

The velocity feedback signal could be achieved via a variety of mechanisms such as providing a coil on the cone, as in FIG. 3, which moves with respect to the magnet of loudspeaker 112 so as to produce a signal indicative of movement of the cone and thereby of the sound being generated by loudspeaker 112. The feedback gain, K is not known and would have to be predetermined before control starts. This gain would be loudspeaker dependent and in general would be on the order of, 100. In addition, the power amplifier 113 is assumed to have a unity power transfer function. The power amplifier 113 is essentially a current amplifier that supplies drive current to the loudspeaker 112 for required actuation.

A major difference between the embodiments of FIGS. 6 and 7 from those of FIGS. 2–4 is that microphone 130-2 is used in both the PW filter 132 and as the error sensor, being placed directly over the control loudspeaker 112. Alternatively, if desired, it could also be located downstream of control loudspeaker 112. The indicated noise source 134 can be either on, or off during Steps 1 and 2. It is assumed that the noise source 134 is on during Step 3. If it is off, the ANC system will be essentially inoperative.

To initiate calibration of loudspeaker 112, switch S3 is closed, switches S4 (FIG. 6 only) and S5 are open and noise source 134 is on. The white noise source 110 (constant amplitude, broadband frequency distribution) supplies a signal to the Loudspeaker Correction Filter (adaptive Finite Impulse Response (FIR) structure) 116, $H_c$, multiplier 129, and Desired Loudspeaker Velocity Response Filter, 117, HD, in loudspeaker adaptive correction block or circuit 190. Circuit 190 has the function of computing the required correction filter 1 16, $H_c$, for the loudspeaker's velocity response based upon a desired response, $H_D$ of filter 117. The output of $H_C$ correction filter 116 is supplied as an input to the servo-loudspeaker via closed switch S3 and adder 138. The servo-output (i.e. velocity of the loudspeaker's cone before gain, K) is fed back to adder 128 negated and summed with the output of the velocity response filter 117. This signal represents an error signal and is the deviation of the actual loudspeaker's cone velocity from the desired loudspeaker's cone velocity. The error signal is combined in a least mean square, LMS, fashion with the input signal from the noise generator 110. Specifically the signal from adder 128 is multiplied with an input signal from noise generator 110 in multiplier 129 and a small constant (not shown), generally referred to as a convergence parameter, which is typically 0.1% of the input power. The process continues until the error signal is reduced to a predetermined small value. After convergence, the $H_C$-filter 116 is copied to filter 116-1 of the FIR controller 192 or 192', as indicated, and filter 116-2 of C-plant identification 194 (FIG. 6, only). FIR controllers 192 and 192'produce outputs that minimizes the sound pressure at microphone or sensor 130-2.

C-plant identification or circuit 194 is the adaptive error path identification circuit whose function is to identify the transfer function, C, that defines the path from the input voltage to filter 116-2 to the output voltage from microphone or sensor 130-2. To initiate C-plant identification in adaptive error path identification filter block or circuit 194 of FIG. 6, switch $S_4$ is closed, switches $S_3$ and S5 are open and white noise source 110 is on. Noise source 110 supplies a signal to adaptive C-filter 140 which is a Transverse Filter (adaptive FIR structure) model of error plant (path from input voltage to servo-loudspeaker to output voltage from microphone 130-2) and to LMS multiplier 141. White noise source 110 directly feeds the input to the servo loudspeaker via closed switch S4, correction filter 116-2, adder 138 and power amplifier 113 which excites the duct 32 with sound energy via the loudspeaker 112. This acoustic signal is sensed by microphone 130-2, negated and summed in adder 142 with the output of filter 140 producing an error signal. The error signal is combined at the multiplier 141 in an LMS fashion (convergence parameter not shown) with the output of the noise generator 110. This process continues until the error signal is reduced to a predetermined, small value. After convergence the C-filter 140 is copied to filter 140-1 of the FIR controller or adaptive digital active noise control filter block or circuit 192, as indicated.

To initiate FIR controller or control filter circuit 192 of FIG. 6 and 192'of FIG. 7, switch S5 is closed and switches S3 and S4 (FIG. 6 only) are open and white noise source 110 is off. Prior to the closing of switch S5 noise from the noise source 134 is propagated down the duct 32 towards microphones 130-1 and 130-2, and the loudspeaker 112. The duct 32 acts as an acoustic waveguide in that the dominant acoustic energy in the duct 32 propagates as plane, acoustic waves (same acoustic pressure in any duct cross-section). At the loudspeaker 112, the acoustic energy associated with the noise source 134, responds to the variation in the normal duct impedance caused by the presence of the loudspeaker 112 (i.e., the loudspeaker has different mass, stiffness and damping properties than that of the duct). Some of the acoustic energy at the loudspeaker 112 is reflected back upstream towards the noise source 134, some is transmitted down the duct 32 and the rest is dissipated as heat through the motion of the loudspeaker's diaphragm. At any downstream duct discontinuity, for example a branch or termination, a similar interaction of the reflection, transmission and dissipation of sound energy occurs. From the physical description given here we see that the sound field, or acoustic pressure, P, in the duct can be described as two plane acoustic waves traveling in a forward, $P_f$, and reverse, $P_r$, direction in the duct. Mathematically, the following equations completely describe the plane-wave, acoustic pressure, P, and acoustic particle velocity, U, at any point in the duct where x, is the longitudinal duct coordinate, j is $\sqrt{-1}$k is the acoustic wavenumber, p is the duct medium density, c is the duct medium speed of sound and the subscripts f and r designate forward and reverse directions, respectively:

$$P = P_f \cdot e^{-j \cdot k^+ \cdot x} + P_r \cdot e^{+j \cdot k^- \cdot x},\ u = U_f \cdot e^{-j \cdot k^+ \cdot x} - U_r \cdot e^{+j \cdot k^- \cdot x}$$

$$U_f = \frac{P_f}{\rho c},\ U_r = \frac{P_r}{\rho c}$$

The constants in the above equation are defined by, $$k^+ = k_c \cdot (1 - M),\ k^- = k_c \cdot (1 + M)$$

-continued $$k_c = \frac{k_0 - j\alpha(M)}{1 - M^2}$$

where:

M =Mach Number and

α(M)=Attenuation Factor.

Note that, the forward pressure, $P_f$, and acoustic particle velocity, $U_f$, waves are in phase (have the same sign) and the reverse pressure, $P_r$, and acoustic particle velocity, $U_r$, wave are in anti-phase (negative sign). The total acoustic pressure is a scalar quantity, that is it has no apparent direction associated with it, only magnitude. In contrast, the acoustic velocity, U, is a vector quantity, and by definition has both direction and magnitude. The positive x-direction was arbitrarily chosen to be represented by waves propagating in a left-to-right fashion in the duct 32, note that the negative sign in the reverse velocity, $U_r$, wave reflects this. The ultimate goal of an ANC system is to cancel all noise which propagates to the receiver. In most cases, this would be at some point located downstream of the ANC system. For these cases, the only offending component of the noise to be canceled is that energy associated with the forward component of the wave propagation. Since all energy propagating in a reverse direction in the duct is assumed to be caused by a reflected component of the forward wave (assuming no downstream sources) at some point in the duct, the reflected wave component would be forced to zero in the absence of any forward propagating component. In addition, by sensing only the forward wave component of the sound field all feedback sound energy from the loudspeaker 112, when active, would be rejected since these sound waves from the loudspeaker 112 are actually reverse sound waves relative to the progressive wave, PW, microphone array.

Since a microphone measures the total acoustic pressure at any point (summation of forward and reverse waves) it would be desirable to devise some means by which only the forward component of the pressure wave is measured. This is exactly accomplished with the PW filter 132.

Notice that the forward acoustic velocity component, $U_f$, is related to the forward pressure component via the specific acoustic impedance quantity, ρc(i.e. $U_f=(P_f/\rho c)$). By having an ideal velocity source (flat frequency response) the acoustic pressure can be exactly replicated. By utilizing a servo mechanism, and correction function $H_c$, the loudspeaker's velocity response essentially becomes ideal.

Referring again to FIGS. 6 and 7, in theory, all that is required for cancellation for the PW, ANC system is to know the appropriate time delay and gain factor for the system. This delay represents the time it takes the forward pressure wave measured at microphone 130-1 to travel to the control loudspeaker 112. Knowing the separation distance between microphone 130-1 and control loudspeaker 112, the delay, τ, can be calculated by, τ=L/c. Where L, is now the distance from microphone 130-1 to control loudspeaker 112 and c, is the wave propagation speed. In addition, the theoretical "gain factor" for control, based upon the above equations describing wave propagation, $$K = \left[\frac{-\rho \cdot c}{2 \cdot AR}\right].$$

In this equation, AR is the area ratio of the duct-to-loudspeaker and assumes a 1-to-1, pressure-to-voltage transfer function for microphones 130-1 and 130-2. The FIGS. 6 and 7 implementations use progressive wave filter 132 which corresponds to PW filter 40 of FIG. 4. Because there could be some variability in both the delay and gain required for control due to flow and high order acoustic effects, the control embodiment of FIR controller 192 or control filter circuit of FIG. 6 uses an adaptive filter 120(A). In addition the previously mentioned "theoretical" gain factor assumes a 1-to-1, pressure-to-voltage transfer function for microphones 130-1 and 130-2. This is generally not the case which makes the adaptive system as described in FIG. 6 desirable over that in FIG. 7. This technique automatically computes the required gain and delay and also accounts for any variation over time in these two quantities. However, for a lower cost and potentially lower performance system, the FIR controller or adaptive noise control filter block or circuit 192'of FIG. 7 may be employed. In FIGS. 6 and 7, microphones 130-1 and 130-2 provide input signals to progressive wave filter 132 and, additionally, microphone 130-2 provides an input to FIR controller or control filter circuit 192 of FIG. 6 and 192'of FIG. 7.

Referring specifically to FIG. 6, the output of filter 132 is supplied as an input to filter 140-1 and adaptive filter 120 of FIR controller or control filter circuit 192. Filter 140-1 provides a first input to multiplier 150. Microphone 130-2 provides a second input to multiplier 150. The output of multiplier 150 is supplied to adaptive filter 120. The output of filter 120 is supplied to filter 116-1 whose output is supplied to speaker 112 via closed switch S5, and adder 138 and power amplifier 113.

Referring now to FIG. 7, the output of filter 132 is supplied via fixed time delay circuit 195 as a first input of gain 152 of FIR controller or control filter circuit 192'. Microphone 130-2 provides a second input to gain 152. The output of gain 152 is supplied to filter 116-1 whose output is supplied to speaker 112 via closed switch S5, and adder 138 and power amplifier 113. In FIG. 7, the error signal supplied by microphone 130-2 is used as input to an analog automatic gain control circuit 152 with a fixed time delay circuit 195. This circuit has the advantage over a fixed gain filter, suggested by the feed gain factor $$K = \left[\frac{-\rho \cdot c}{2 \cdot AR}\right],$$

in that it can respond, in a DC fashion, to any variation in loudspeaker or microphone sensitivity. This system is not as robust as that of FIG. 6 in that it cannot respond to individual frequency variations and therefore its performance may be less than that of FIG. 6. However, this system would cost dramatically less than that of FIG. 6.

The systems of FIGS. 6 and 7 described above offer a number of advantages over prior art systems in that they permit reducing the distance requirements for the installation. The sensing microphones 30-1 and 30-2 can be separated by a relatively small distance, e.g. ⅛ of the wavelength of the highest frequency of interest for a purely analog system located within a duct. The sensing of the movement of cone 133 via coil 13-7 permits the determination of the sound being produced by the driving structure as opposed to knowing the input signal and sensing the results thereof after the fact. For the analog version, all components of the ANC system including microphones, servo-loudspeaker and ancillary electronics are assumed to be "ideal". That is having a unity input-to-output voltage transfer function. In the case of a digital system, adaptive filters are used to compensate for uncertainties, i.e. non-ideal transfer functions, that can occur in an actual ANC system.

In both the digital and analog PW systems of FIGS. 6 and 7, respectively, microphone 130-2, is used to monitor and provide feedback information on system performance (error sensor) - it also provides input to the PW filter 132. Both systems would tend to minimize the overall pressure at microphone 130-2. This in essence forces a pressure-equal-zero condition at the loudspeaker 112, whereby all transmitted sound energy would tend to zero.

Although preferred embodiments of the present invention have been specifically illustrated and described, other changes will occur to those skilled in the art. It is therefore intended that the scope of the present invention is to be limited only by the scope of the appended claims.

What is claimed is:

1. A noise canceling system for an air distribution structure comprising:

duct means for delivering air;

a source of noise located with respect to said duct means so as to transmit noise into said duct means as a forward component which is subject to reflection due to coaction with said duct means to produce a reflected component whereby noise from said source of noise can be present in said duct means as both a forward component and a reflected component;

sensing means located in said duct means;

said sensing means includes a pair of sensors in a spaced relationship along said duct means relative to said source of noise;

noise canceling means located with respect to said duct means so as to transmit a canceling noise into said duct means;

circuitry connected to said sensing means and said noise canceling means and including means for distinguishing between said forward component and said reflected component and for producing an output representative of only said forward component and means for driving said noise canceling means so as to produce noise corresponding only to said forward component.

2. The system of claim 1 wherein said means for distinguishing between said forward component and said reflected component is a progressive wave filter.

3. The system of claim 1 wherein said means for distinguishing between said forward component and said reflected component is a forward pressure wave approximation filter.

4. The system of claim 1 wherein said circuitry includes means for sensing a parameter corresponding to actual output of said noise canceling means and means for feeding back said sensed output to said means for driving said noise canceling means so as to adjust said means for driving said noise canceling means.

5. The system of claim 1 wherein said circuitry provides a time delay corresponding to the time necessary for noise from said source of noise to travel between said sensing means and said noise canceling means.

6. The system of claim 1 further including:

a second sensing means located in said duct means at a location such that said noise canceling means is located intermediate said second sensing means and said source of noise;

said second sensing means being connected to said circuitry means so as to provide a signal representative of the result of interaction between noise from said source of noise and said noise canceling means;

said circuitry including means responsive to said signal representative of the result of interaction between noise from said source of noise and said noise canceling means to adjust said means for driving said noise canceling means.

7. The system of claim 1 wherein one of said pair of sensors is located opposite said noise canceling means, and said one of said pair of sensors is connected to error sensing means which forms a part of said circuitry.

8. The system of claim 1 wherein said pair of sensors in a spaced relationship relative to said source of noise is located upstream of said noise canceling means.

9. The system of claim 1 wherein: said circuitry includes a progressive wave filter connected to said pair of sensors and a finite impulse response controller connected to one of said pair of sensors and said progressive wave filter and providing an output to said noise canceling means.

10. The system of claim 9 further including:

a loudspeaker correction circuit including a white noise source, an adaptive transverse filter, and a desired loudspeaker velocity response transfer function; and means for selectively connecting said calibration circuit to said noise canceling means and disabling said output of said controller.

11. The system of claim 10 further including:

a an adaptive error path identification circuit including an adaptive transverse filter and connected to said white noise source; and means for selectively connecting said calibration circuit to said noise canceling means and disabling said output of said controller.

12. The system of claim 11 wherein said controller includes a filter copied from said adaptive transverse filter of said identification circuit.

13. The system of claim 12 wherein said controller includes a filter copied from said adaptive transverse filter of said speaker calibration circuit.

14. The system of claim 10 wherein said controller includes a filter copied from said adaptive transverse filter of said speaker calibration circuit.

* * * * *